(12) United States Patent
Belasco et al.

(10) Patent No.: US 6,818,410 B2
(45) Date of Patent: Nov. 16, 2004

(54) METHODS OF ISOLATING RNA-BINDING PROTEINS AND COMPOSITIONS RELATED TO THE SAME

(75) Inventors: Joel Belasco, Scarsdale, NY (US); Stefan Danner, Kiefersfelden (DE)

(73) Assignee: New York University, New York, NY (US)

( * ) Notice: Subject to any disclaimer, the term of this patent is extended or adjusted under 35 U.S.C. 154(b) by 0 days.

(21) Appl. No.: 10/156,708

(22) Filed: May 28, 2002

(65) Prior Publication Data

US 2004/0175697 A1 Sep. 9, 2004

Related U.S. Application Data

(60) Provisional application No. 60/293,971, filed on May 29, 2001.

(51) Int. Cl.[7] .............................. C12Q 1/68; C12Q 1/00; C12N 15/09; C12N 15/00; C07H 21/04
(52) U.S. Cl. ................................ 435/7.1; 435/4; 435/6; 435/235.1; 435/252.3; 435/320.1; 435/69.7; 435/69.1; 435/91.1; 536/23.1; 536/23.4; 536/24.1
(58) Field of Search ...................... 435/4, 6, 7.1, 235.1, 435/320.1, 69.1, 69.7, 91.1, 252.3; 536/23.1, 23.4, 24.1

(56) References Cited

U.S. PATENT DOCUMENTS 5,223,409 A 6/1993 Ladner et al.
5,403,484 A 4/1995 Ladner et al.

OTHER PUBLICATIONS

Wan et al. Journal of Biological Chemistry, vol. 276, No. 10, pp. 7681–7688, Mar. 09, 2001.*
Danner et al. Proceedings of the National Acadamy of Sciences, USA. Vol. 98, No. 23, pp. 12954–12959, Nov. 06, 2001.*
Jessen et al., EMBO J., 10:3447–3456 (1991).
Laird–Offringa et al., Methods Enzymol., 267:149–168 (1996).
Laird–Offringa et al., Proc. Natl. Acad. Sci USA, 92:11859–11863 (1995).
Lowman, Annu. Rev. Biophys., Biomol. Struct., 26:401–424 (1997).
Martin et al., EMBO J., 16:769–778 (1997).
Nakielny et al., EMBO J., 18:1982–1995 (1999).
Rodi et al., Curr. Opin. Biotechnol., 10:87–93 (1999).
Wang et al., Genes Dev., 10:3028–3040 (1996).

* cited by examiner

Primary Examiner—Gerry Leffers
(74) Attorney, Agent, or Firm—Klauber & Jackson (57) ABSTRACT

The present invention discloses a general in vitro method for isolating proteins that bind to specific RNA regulatory elements. The method employs a lyt-lys bacteriophage display library and a host bacterial cell that has been modified so as to release minimal-to-no RNase activity in the corresponding phage lysate.

11 Claims, 4 Drawing Sheets

```
        U U
      U     C
       U A
        C G
        C G
        C G
        C G
        G C
   AAAAG  CACC
```

METHODS OF ISOLATING RNA-BINDING PROTEINS AND COMPOSITIONS RELATED TO THE SAME

RELATED PATENT APPLICATIONS

This application claims priority under 35 USC §119(e) to provisional patent application U.S. Ser. No. 60/293,971 filed May 29, 2001, herein specifically incorporated by reference in its entirety.

GOVERNMENTAL SUPPORT

The research leading to the present invention was supported, at least in part, by the National Institutes of Health Grant No. R01 GM55624. Accordingly, the U.S. Government may have certain rights in the invention.

FIELD OF THE INVENTION

The present invention relates generally to a method of isolating RNA-binding proteins. Particular modified bacterial host cells that are used in these methods are also provided.

BACKGROUND OF THE INVENTION

RNA-binding proteins (RNA-BPs) play a key role in a variety of post-transcriptional regulatory processes, including RNA processing, nucleocytoplasmic transport, translation, and mRNA decay. Moreover, a burgeoning body of evidence has implicated a number of RNA-BPs in the genetic etiology of human diseases such as fragile X mental retardation (Ashley et al. (1993) Science 262:563–566), paraneoplastic neurologic disorders (Musunuru et al. (2001) Annu. Rev. Neurosci. 24:239–262), and spinal muscular atrophy (Fischer et al. (1997) Cell 90:023–1029), as well as in many microbial infections, including AIDS (Cullen (1998) Cell 93:685–692) and influenza (Garcia-Sastre 2001) Virology 279:75–384).

An essential step in elucidating the regulatory mechanism of a given RNA element is to identify and characterize the protein(s) that binds to this element and mediates its effect. Characterization of such an RNA-BP is most readily accomplished by cloning its cDNA. Traditionally, this has been achieved by protein purification, peptide microsequencing, and cDNA amplification with PCR primers designed on the basis of the amino acid sequence information. This labor-intensive strategy requires an enormous effort and can be particularly difficult in the case of RNA-BPs that are present at a relatively low cellular concentration. Some genetic screening methods have been developed to facilitate the cloning of RNA-BP cDNAs, most notably the yeast three-hybrid system (SenGupta et al. (1996) Proc. Natl. Acad. Sci. USA 93:8496–8501; Putz et al. (1996) Nucleic Acids Res. 24:4838–4840) and plaque-lift analysis (Qian et al. (1993) Anal. Biochem. 212: 47–554; Sagesser et al. (1997) Nucleic Acids Res. 25:3816–3822). Both techniques have allowed the cloning of previously unidentified RNA-BPs (Wang et al. (1996) Genes Dev. 10:3028–3040; Martin et al. (1997) EMBO J. 16:769–778; Zhang et al. (1997) Nature 390:477484; Denti et al. (2000) Nucleic Acids Res. 28:1045–1052).

However, several limitations may interfere with the general applicability of these procedures. For example, when using the three-hybrid system, the RNA-protein interaction takes place in vivo, where it can be influenced by a multitude of cellular parameters. False-positive clones frequently predominate, and these must be eliminated by additional time-consuming screening steps. For their part, plaque-lift assays are often severely hampered by inefficient or non-specific binding of the radiolabeled RNA probe to the filter-bound plaques.

There is a need to design methodology that can be used to isolate new RNA-binding proteins. In addition, there is a need to construct particular modified host cells useful in performing such methodology.

SUMMARY OF THE INVENTION

The present invention provides a general in vitro method for isolating proteins that bind to specific RNA regulatory elements. The method employs a lyt-lys bacteriophage display library and a host bacterial cell that has been modified so as to release minimal-to-no RNase activity in the corresponding phage lysate. In a particular embodiment, the host cell has been modified to lack one particular ribonuclease activity. In a preferred embodiment, the host cell has been modified to lack one particular ribonuclease activity by deleting a particular gene that encodes the ribonuclease responsible for that activity.

In a particular embodiment, that ribonuclease activity is one that is otherwise responsible for the majority (or preferably all) of the RNase activity in the phage lysate. In another embodiment the particular ribonuclease activity is due to a ribonuclease that is not required for host cell viability. In a preferred embodiment, the ribonuclease activity is both one (i) that is otherwise responsible for the majority (or all) of the RNase activity in the phage lysate, and (ii) that ribonuclease activity is due to a ribonuclease that is not required for host cell viability.

In one embodiment, the bacterial host is a modified Gram negative bacterium. In a more specific embodiment, the modified bacterium is an enteric bacterium (i.e., belonging to the Enterobacteriaceae Family). In one such embodiment the modified bacterial host is Salmonella. In another such embodiment the modified bacterial host is Shigella. In still another embodiment, the modified bacterial host is Yersinia. In yet another embodiment, the modified bacterial host is Enterobacter. In still another embodiment, the modified bacterial host is Klebsiella. In a preferred embodiment, the modified bacterial host is *Escherichia coli*. Preferably the modified host bacterial cell had been modified to lack a periplasmic ribonuclease.

In a particular embodiment exemplified below, a specific *E. coli* strain (BLT5615, Novagen) is modified so that it lacks the gene for a major nonspecific *E. coli* ribonuclease, Rnase I (amino acid sequence of SEQ ID NO:1). This novel strain, has the T genotype F$^-$ rna ompT gal hsdS$_B$ (r$_B$–m$_B$–) dcm lac pAR5615 (amp$^R$), herein known as RNA5615, and is part of the present invention.

By genetically deleting the RNase I (rna) gene from strain BLT5615, a variant *E. coli* strain (RNA5615) as been created which, when used with the T7 SELECT DISPLAY SYSTEM (U.S. Pat. No. 5,223,409 Issued Jun. 29, 1993 and U.S. Pat. No. 5,403,484 Issued Apr. 4, 1995, the contents of which are herein specifically incorporated by reference in their entireties) produces crude phage lysates that do not degrade RNA, even after prolonged incubation in the presence of magnesium ions. Consequently, phages that bind to an interesting RNA target can be isolated from crude phage lysates without first having to be purified by additional steps such as by sucrose gradient centrifugation.

The present invention therefore provides methods of identifying nucleic acids that encode RNA-binding proteins that bind to specific RNA regulatory elements. Once these nucleic acids are identified, the corresponding RNA binding proteins can be readily determined. One such method comprises inserting a cDNA into a lyt-lys phage cloning vector encoding the major capsid protein of the lyt-lys phage such that a heterologous protein encoded by the cDNA is expressed as a fusion protein with capsid protein when the cloning vector is packaged in a phage capsid. Further, the fusion protein is constructed such that the heterologous protein is accessible to the buffer and/or solvent when the resulting capsid is in solution. This ensures that the heterologous protein is accessible for binding an external ribonucleic acid (see FIG. 1).

The lyt-lys cloning vector is then packaged in a phage capsid in a host bacterial cell under conditions in which the phage capsid lyses the host cell after being packaged, thus forming a lysate. A host bacterial cell is used which previously had been modified so as to release minimal-to-no RNase activity in the corresponding phage lysate. This relatively RNase-free lysate is then contacted with a ribonucleotide that comprises a specific RNA regulatory element. When a phage capsid comprises a nucleic acid that encodes a heterologous protein that binds the specific RNA regulatory element, the phage capsid binds to the ribonucleotide forming an RNAapsid complex. The ribonucleotides and the RNA-capsid complexes are next separated from the lysate. The isolated capsids can then be used to infect fresh host bacterial cells leading to the formation of a fresh lysate. The fresh lysate can then be contacted with fresh ribonucleotides comprising the specific RNA regulatory element. Indeed, this in vitro selection process is preferably iterative. In any case, the nucleic acid encoding the heterologous protein of the phage capsid of the final RNA-capsid complex isolated is identified. This nucleic acid will encode an RNA-binding protein that binds to the specific RNA regulatory element.

In one particular embodiment of this method, the lyt-lys bacteriophage is T7, the cloning vector is a T7 cloning vector, the major capsid protein is T7 capsid protein 10B, and the host cell is $E.$ coli RNA5615 having the genotype F$^-$ rna ompT gal hsdS$_B$ (r$_B$–m$_B$–) dcm lac pAR5615 (amp$^R$).

The present invention further provides kits for identifying a nucleic acid that encodes an RNA-binding protein that binds to a specific RNA regulatory element. One such kit comprises a T7 cloning vector encoding T7 capsid protein 10B and an $E.coli$ cell having the genotype F$^-$ rna ompT gal hsdS$_B$ (r$_B$–m$_B$–) dcm lac pAR5615 (amp$^R$). In a preferred embodiment a streptavidin-coated paramagnetic bead is also included. In a particular embodiment the kit further comprises a protocol for performing the identification.

The present invention to provide an in vitro method for isolating RNA-binding proteins through the use of a phage display library and either undegraded or minimally degraded ribonucleic acids that comprise RNA regulatory elements or protein binding portions thereof.

Further, the present invention provides a bacterial host cell that has been modified so as to not encode an active periplasmic RNase that degrades RNA regulatory elements or protein binding portions thereof.

These and other aspects of the present invention will be better appreciated by reference to the following drawings and Detailed Description.

BRIEF DESCRIPTION OF THE DRAWINGS

FIG. 1 shows the in vitro selection of RNA-BP cDNAs using T7 phage display. An RNA-BP cDNA is inserted into a T7 cloning vector and packaged in a phage capsid to generate a recombinant phage in which the RNA-BP is displayed on the surface as a C-terminal fusion to the T7 capsid protein 10B. The resulting phage is allowed to bind to the RNA bait, which itself is annealed to a biotinylated DNA oligonucleotide. RNA-bound T7 phage are captured on streptavidin-coated paramagnetic beads, separated from other members of the phage mixture with a magnet, and used to infect $E.$ coli without prior release from the beads. After replication, the phage progeny can be subjected to additional rounds of selection.

FIG. 2 is a schematic representation of the three RNA stem-loop structures used in these experiments. Nucleic acid sequences of U1hpII (SEQ ID NO: 12); U1hpII$_{mut1}$ (SEQ ID NO: 13) and U2hpIV (SEQ ID NO: 14) are shown. The previously determined affinity of each for U1A ($K_d$) is indicated (O'Connor et al. (1997) RNA 3:1444–1455). The nucleotide changes in U1hpII$_{mut1}$ and U2hpIV that are responsible for the diminished affinity of U1A for these stem-loops are highlighted. In addition to the stem-loop structures shown, each RNA contained 4 or 6 additional base pairs at the bottom of the stem, a short 5' leader, and a 3' tail that had been annealed to a complementary 5'-biotinylated DNA oligonucleotide prior to selection.

DETAILED DESCRIPTION OF THE INVENTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only the appended claims.

As used in this specification and the appended claims, the singular forms "a", "an", and "the" include plural references unless the context clearly dictates otherwise. Thus for example, references to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein ale incorporated herein by reference to disclose and described the methods and/or materials in connection with which the publications are cited.

Definitions

As used herein a "lyt-lys bacteriophage" or "lyt-lys phage" is a bacteriophage that is either a lytic bacteriophage or a lysogenic bacteriophage. More particularly a "lyt-lys phage" must lyse its host cell in order to be released from that host cell. Therefore, lyt-lys phages include lysogenic (or temperate) bacteriophage such as the bacteriophage lambda and "lytic bacteriophage" such as the lytic T phages (e.g. T1, T4, and T7). On the other hand, filamentous bacteriophage such as f1, fd and M13, which do not lyse their host cell are not lyt-lys phage.

An RNA-binding protein (RNA-BP) is a protein that binds to a particular site of an RNA Preferably an RNA-BP binds to an RNA regulatory element.

The terms "fusion protein" and "fusion peptide" are used interchangeably and encompass "chimeric proteins and/or chimeric peptides" and fusion "intein proteins/peptides". An RNA-binding protein fusion protein of the present invention comprises at least a portion of a RNA-binding protein joined via a peptide bond to at least a portion of another protein or peptide. For example fusion proteins can comprise a marker protein (e.g., green fluorescent protein) or peptide, and/or a protein or peptide that aids in the isolation and/or purification of a RNA-binding protein of the present invention. In addition, a "fusion protein" of the present invention can comprise a putative or known RNA-binding protein or fragment thereof and a capsid protein from a bacteriophage. In this case, as used herein, the putative RNA-binding protein can be referred to herein, as a heterologous protein.

A molecule is "antigenic" when it is capable of specifically interacting with an antigen recognition molecule of the immune system, such as an immunoglobulin (antibody) or T cell antigen receptor. An antigenic polypeptide contains at least about 5, and preferably at least about 10 or more amino acids. An antigenic portion of a molecule can be that portion that is immunodominant for antibody or T cell receptor recognition, or it can be a portion used to generate an antibody to the molecule by conjugating the antigenic portion to a carrier molecule for immunization. A molecule that is antigenic need not be itself immunogenic, i.e., capable of eliciting an immune response without a carrier.

As used herein the terms "approximately" and "about" are used to signify that a value is within twenty percent of the indicated value i.e., a polypeptide fragment containing "approximately" 150 amino acid residues can contain between 120 and 180 amino acid residues.

A "small organic molecule" is an organic compound [or organic compound complexed with an inorganic compound (e.g., metal)] that has a molecular weight of less than 3 kilodaltons.

As used herein the term "binds to" is meant to include all such specific interactions that result in two or more molecules showing a preference for one another relative to some third molecule. This includes processes such as covalent, ionic, hydrophobic and hydrogen bonding but does not include non-specific associations such as solvent preferences.

The term "gene" refers to an assembly of nucleotides that encodes a polypeptide, and includes cDNA and genomic DNA nucleic acids. A nucleic acid encoding an RNA binding protein of the present invention is not used herein as a synonym of the corresponding naturally occurring gene which contains all of the introns and regulatory sequences, e.g., promoters, present in the natural genomic DNA. Rather, a nucleic acid encoding a particular polypeptide can minimally contain just the corresponding coding nucleotide sequence for the polypeptide. In a particular embodiment, the nucleic acid does not contain at least one of the introns or regulatory sequences of the corresponding gene.

A "heterologous nucleotide sequence" as used herein is a nucleotide sequence that is added to a nucleotide sequence encoding a putative or known RNA binding protein (and/or encoding a capsid protein) of the present invention by recombinant methods to form a nucleic acid that is not naturally formed in nature. Such nucleic acids can encode chimeric and/or fusion proteins. Thus the heterologous nucleotide sequence can encode peptides and/or polypeptides which contain regulatory and/or structural properties. In another such embodiment the heterologous nucleotide can encode a polypeptide or peptide that functions as a means of detecting the polypeptide or peptide encoded by the nucleotide sequence of the present invention after the recombinant nucleic acid is expressed. In still another such embodiment the heterologous nucleotide can function as a means of detecting a nucleotide sequence of the present invention. A heterologous nucleotide sequence can comprise non-coding sequences including restriction sites, regulatory sites, promoters and the like.

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmaids, and chromosomes. In discussing the structure of particular double-stranded DNA molecules, sequences may be described herein according to the normal convention of giving only the sequence in the 5 prime to 3 prime direction along the non-transcribed strand of DNA (i.e., the strand having a sequence homologous to the mRNA). However, unless specifically stated otherwise, a designation of a nucleic acid includes both the non-transcribed strand referred to above, and its corresponding complementary strand. Such designations include SEQ ID NOs:. A "recombinant DNA molecule" is a DNA molecule that has undergone a molecular biological manipulation.

A DNA "coding sequence" is a double-stranded DNA sequence that is transcribed and translated into a polypeptide in a cell in vitro or in vivo when placed under the control of appropriate regulatory sequences. The boundaries of the coding sequence are determined by a start codon at the S prime (amino) terminus and a translation stop codon at the 3 prime (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3 prime to the coding sequence.

Transcriptional and translational control sequences are DNA regulatory sequences, such as promoters, enhancers, terminators, and the like, that provide for the expression of a coding sequence in a host cell. In eukaryotic cells, polyadenylation signals are control sequences.

A "promoter" is a DNA regulatory region capable of binding RNA polymerase in a cell and initiating transcription of a downstream (3 prime direction) coding sequence.

For purposes of defining the present invention, the promoter is bounded at its 3 prime terminus by the transcription initiation site and extends upstream (5 prime direction) to include the minimum number of bases or elements necessary to initiate transcription at levels detectable above background. Within the promoter will be found a transcription initiation site (conveniently defined for example, by mapping with nuclease S1), as well as protein binding domains (consensus sequences) responsible for the binding of RNA polymerase.

A coding sequence is "under the control" of transcriptional and translational control sequences in a cell when RNA polymerase transcribes the coding sequence into mRNA, which is then trans-RNA spliced and translated into the polypeptide encoded by the coding sequence.

A "signal sequence" is included at the beginning of the coding sequence of a polypeptide to be expressed on the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of polypeptides native to eukaryotes and prokaryotes, and are often functional in both types of organisms.

General Description of the Invention

RNA-binding proteins are central to postanscriptional gene regulation and play an important role in a number of major human diseases. Cloning such proteins is a crucial but often difficult step in elucidating the biological function of RNA regulatory elements. Therefore, the present invention provides methods of isolating RNA-binding partners (e.g., proteins that bind RNA) of naturally occurring RNA sequences (e.g., RNA regulatory elements). More particularly, the method involves an in vitro selection from a bacteriophage display library of cellular cDNAs which allows a protein ligand of virtually any RNA regulatory element to be readily cloned, provided that the protein can bind as a monomer or homomultimer. Importantly, the methodology provides a stable environment for the RNA regulatory elements used as bait to bind their RNA-binding partners.

Thus, one critical aspect of the methods provided by the present invention is the ability to overcome the inherent problem of the degradation of RNA regulatory elements in bacterial cell lysates. Therefore, although the methodology of the present invention is capable of being used with any bacteriophage-bacterial host system, the present invention is particularly advantageous when used with a lyt-lys phage, since the lysis of the host cell results in the release of ribonucleases (Rnases). In addition, the methodology is preferably performed with a Gram-negative bacterial host (e.g., an enteric bacterium) in which the RNase(s) that is inhibited, inactivated and/or removed is a periplasmic RNase (e.g., RNase I from E. coli).

The use of a lyt-lys phage vector circumvents a major drawback encountered with attempts to display cDNA libraries on M13, namely incomplete representation of the protein library on the phage surface. Many proteins cannot be displayed on M13 because merely fusing them to a signal peptide is insufficient to allow their export through the bacterial inner membrane, as required for assembly into phage particles. There is no such impediment to protein display for lyt-lys phages such as M phages, which assemble within the cytoplasm. Furthetmore, joining cDNAs to the promoterdistal end of T7 gene 10, which has only a single translated DNA junction, is significantly more likely to yield in-frame gene fusions than using M13 cloning vectors in which cDNAs must be sandwiched between vector sequences that encode a signal peptide and the M13 capsid protein (a total of two translated junctions).

One problem of using lytic phage display vectors to clone RNA-BPs is that the phage preparations become contaminated with bacterial ribonucleases released upon phage-induced cell lysis. These ribonucleases degrade the RNA used as bait during selection. The present invention solves this problem by the use of a host cell that lacks these interfering nucleases. In a particular embodiment, exemplified below, a new E. coli host strain that lacks the periplasmic ribonuclease RNase I is employed. T7 phages grown in this strain are free of significant ribonuclease contamination.

Another advantage of lyt-lys phage display (e.g., T7 phage display) for isolating specific RNA-BP cDNAs is the speed of the selection process. Indeed, since iterative in vitro selection is preferred, and two cycles of selection can be performed per day, it is possible to isolate a unique cDNA clone in as little as 2–3 days. This time frame is significantly shorter than is required for other cloning methods. A second important benefit of phage display is that selection is performed in vitro, where conditions for the RNA-protein interaction can be controlled precisely. In contrast, the three-hybrid cloning system relies upon screening in yeast cells, where the binding environment is poorly defined and selection is susceptible to interference by unknown cellular parameters. Consequently, the selection of false positive clones, which is a significant problem for the yeast three-hybrid system (9, 10, 13–15), is far less likely in the case of lyt-lys phage display (e.g., T7 phage display).

The present invention therefore provides methodology that makes it easier to clone proteins that specifically bind RNA elements of interest. Although a bacteriophage T7 display library is exemplified other lyt-lys phages can also be used. Care should be taken to identify the major capsid protein of the individual phage strain. In addition, it is preferable to initially determine whether it is the C-terminus or the N-terminus of the major capsid protein that points outward from the capsid, and is thereby, the end to attach (through genetic engineering) the fused putative or known RNA-BPs.

Another important parameter that can be controlled during in vitro selection is the concentration of the RNA bait. As the binding affinity of a novel RNA-BP is not likely to be known prior to its cloning and characterization, it is initially advisable to use a moderately high RNA concentration (e.g., 100 nM) for selection. The success in using the low-affinity ligand U2hpIV to isolate U1A phage from a cDNA library disclosed below indicates that an RNA bait concentration as low as one-tenth of the $K_d$ is sufficient. It should be noted that the ease with which a cDNA clone can be isolated will depend not only on its equilibrium binding affinity for the RNA bait, but also on its rate of dissociation from the ligand during subsequent steps in which bound phages are immobilized on beads and unbound phages are washed away.

Thus, in a particular embodiment of the present invention, a rapid and broadly applicable in vitro genetic selection method has been developed based on T7 phage display, see Example below. Using hairpin II of U1 small nuclear RNA (U1hpII) or the 3' stem-loop of histone mRNA as bait T7 phage that display either the spliceosomal protein U1A or the histone stem-loop binding protein from a lung cDNA phage library containing more than $10^7$ independent clones, could be selectively amplified. The use of U1hpII mutants with various affinities for U1A revealed that this method allows the selection of proteins that bind their cognate RNA targets with even relatively weak affinities ($K_d$ as high as the micromolar range). Experiments with a mixture of recombinant phages displaying U1A or the closely related protein U2B" demonstrated that addition of a competitor RNA can suppress selection of a protein with a higher affinity for a given RNA target, thereby allowing the preferential amplification of a lower-affinity protein. Together, these findings suggest that a lyt-lys phage (e.g., T7 phage) display can be used to rapidly and selectively clone virtually any protein that binds a known RNA regulatory element, including those that bind with low affinity or that must compete for binding with other proteins. By targeting specific mRNAs, such customized RNA-BPs are valuable tools for manipulating gene expression.

Specific Embodiments

A potential, but heretofore untested method for rapidly cloning RNA-BP cDNAs is by phage display (Lowman (1997) Annu. Rev. Biophys. Biomol. Struct. 26:401424; Rodi et al. (1999) Curr. Opin. Biotechnol. 10:87–93), which combines high selectivity with the rapid amplification of a particular clone. Phage display is a powerful genetic selection method that allows the rapid in vitro isolation of proteins or protein variants that have desirable ligand-binding or catalytic properties, starting from a cDNA library or a combinatorial library of gene mutants. Indeed, previous mutational studies of RNA-BPs using the filamentous bacteriophage M13 phage display (Lurd-Offringa (1995) Proc. Natl. Acad. Sci. USA 92:11859–11863; Laird-Offringa et al. (1996) Methods Enzymol. 267:149–168) have demonstrated the utility of this method for identifying which protein residues of a known RNA-BP are critical for its RNA-binding affinity.

However, a pivotal drawback of using M13 phage display for cloning RNA-BPs from a cDNA library is that the nonlytic propagation mechanism of this phage requires that all components of the phage particle be exported through the bacterial inner membrane prior to phage assembly. Consequently, only proteins that are capable of such export can be displayed on the M13 phage capsid. This property depends not only on the presence of a signal peptide, which can be provided by the cloning vector, but also on the length, sequence, and folding characteristics of each protein to be displayed. Therefore, only a subset of proteins encoded by a given cDNA library are capable of display on M13 phage.

The limitation of the prior art protein display on M13 is obviated, as described below, by using a lyt-lys phage vector in which phage assembly takes place entirely in the cytoplasm. Indeed, phage display vectors based on the lytic phage T7 have been recently developed, e.g., Novagen, that eliminate the need for protein export. Furthermore, the potential of the phage libraries to display all types of RNA-binding domains makes such display vectors superior to M13 for isolating novel protein variants with customized RNA-binding specificities from combinatorial libraries of RNA-BP mutants.

However, unlike M13 phage, which replicate without lysing the host cell, RNA-BP display on lytic phage posed one serious new problem. Bacterial ribonucleases are released upon cell lysis thereby contaminating the T7 phage preparations, and degrading the RNA used as bait for selection. One potential solution was to purify the phage particles from the lysates by sucrose gradient centrifugation. However, this procedure is very time-consuming process.

As disclosed herein, the degradation of the RNA bait was overcome through the construction of a novel ribonuclease-deficient host bacterial strain to minimize contamination by cellular ribonucleases. More particularly, the ribonuclease activity removed from the host bacterial strain was RNase I. RNase I is not only responsible for the majority of the RNase activity in the lysate, but it is also not essential for the viability of the intact host cell. Indeed, with this crucial modification, it was possible to demonstrate the effectiveness of T7 phage display as a strategy for the selective isolation of RNA-BPs from a complex cDNA library. As demonstrated herein, this new procedure proved to be faster and more specific s than previous methods for cloning RNA-BP cDNAs.

Display of the N-terminal RNA-binding domain of U1A on T7phage: As a model system for the development of a method for rapidly cloning RNA-BPs from T7 phage display libraries, the well-studied interaction of the spliceosomal protein U1A with its RNA target, the U1 snRNA stem-loop U1hpII was chosen (Scherly et al. (1989) EMBO J. 8:4163–4170; Jessen et al. (1991) EMBO J. 10:3447–3456; Allain et al. (1997) EMBO J. 16:5764–5774). U1A comprises two tandem RNA-binding domains belonging to the RRM (RNA recognition motif) family (Burd et al. (1994) Science 265:615–621; Nagai et al. (1995) Trends Biochem. Sci. 20:235–240). Since the amino-terminal RRM domain, comprising U1A residues 1–101, alone is responsible for binding U1hpII (Lutz-Freyermuth et al. (1990) Proc. Natl. Acad. Sci. USA 87:6393–6397), the initial experiments were performed with this single dornain. A human cDNA fragment encoding this U1A domain was inserted together with a FLAG epitope tag into the phage cloning vector T7Select1-2c (Novagen™) to generate a gene fusion encoding the amino-terminal half of U1A fused to the carboxy terminus of the phage capsid protein 10B (FIG. 1) via a peptide tether ten residues in length. The presence of U1A on the surface of the recombinant phage was confirmed by Western analysis of phage lysates, using anti-FLAG or anti-U1A antibodies.

Figure 1:
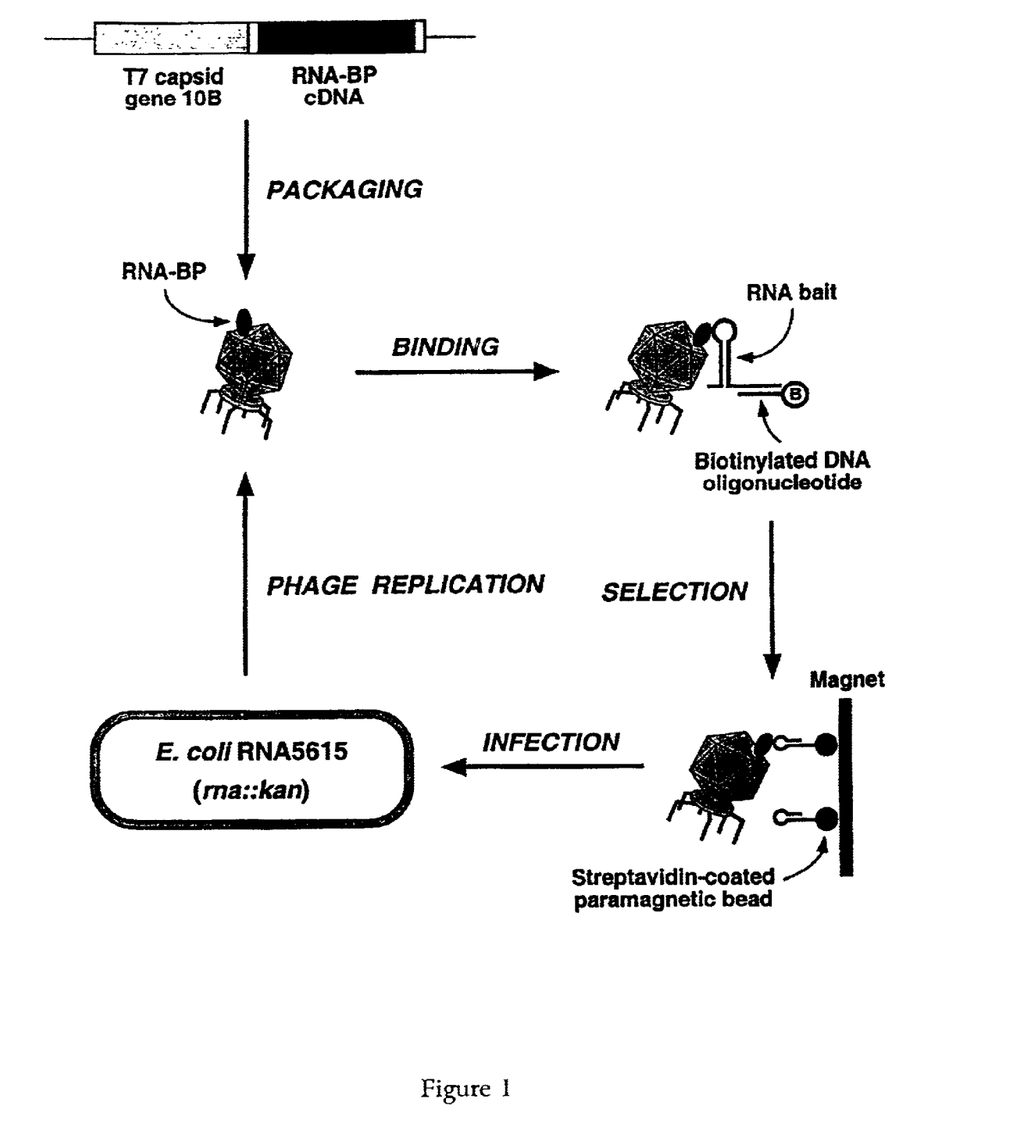

Stability of RNA in phage tysates: U1hpII RNA was synthesized for use as bait by in vitro transcription, and hybridized via its 3' tail to a complementary 5'-biotinylated DNA oligonucleotide. The biotin modification made it possible to couple the RNA/DNA duplex to streptavidin-coated paramagnetic beads, thereby providing a selective means for isolating any recombinant T7 phage that can bind the bait RNA from a phage pool (FIG. 1).

A critical parameter for the success of this cloning method was the stability of the bait RNA in the phage lysate. Unlike M13 phage, which grow nonlytically and are exported from intact E. coli cells, the lytic release of T7 phage from E. coli contaminate such lytic phage preparations with host-cell ribonucleases which are released upon the lysis of the cell. Consistent with this prediction, incubating U1hpII RNA with T7 phage grown in E. coli BLT5615 cells resulted in the degradation of more than 90% of the RNA within 60 min at room temperature (results not shown). Such RNA degradation seriously complicates efforts to select T7 phage that display a protein with RNA-binding properties of interest. Prior purification of the phage particles via polyethylene glycol precipitation and CsCl step-gradient centrifugation resulted in only a minimal improvement in RNA stability.

It was therefore investigated whether RNA degradation in T7 phage lysates could be prevented by genetically inactivating one or more ribonucleases of the host strain. RNase I was chosen as an initial target because it is a major, yet nonessential, ribonuclease activity in E. coli (Nicholson (1999) FEMS Microbiol. Rev. 23:371–390; Jain C et al. (2001) Mol. Cell 7: 603–614). The RNase I gene (rna) of strain BLT5615 was disrupted by P1 transduction to generate a new *E. coli* host strain (RNA5615) lacking this ribonuclease. In contrast to the extensive RNA degradation observed in phage lysates prepared from the original host strain, RNA was almost completely stable in phage lysates of the RNase I-deficient strain (results not shown). Even in the presence of magnesium ions, which can activate many ribonucleases, RNA remained intact in the phage lysates prepared from RNA5615. These findings demonstrate the usefulness of this Rnase I-deficient host strain for T7 phage display studies of both magnesium-dependent and magnesium-independent RNA-protein interactions.

Affinity selection of U1A-displaying phage: As an initial test of the feasibility of using T7 phage display to clone RNA-BP cDNAs, a pilot experiment was performed in which recombinant U1A-displaying phage were isolated from a $10^6$-fold excess of T7 phage lacking an insert (bare phage). The phage mixture (~$2 \times 10^9$ pfu) was incubated with U1hpII (FIG. 2) at an RNA concentration (100 nM) well above the $K_d$ of the U1A-U1hpII complex (0.33 nM) (Laird-Offringa et al. (1995) Proc. Natl. Acad. Sci. USA 92:11859–11863). The RNA-bound phage were recovered by addition of streptavidin-coated paramagnetic beads, washed twice, and amplified by growth in *E. coli*. The new phage lysate was then titered and subjected to another round of selection. In all, four selection cycles were performed. After each round, the phage population was analyzed by PCR using phage-specific primers flanking the U1A cDNA insert. U1A-displaying phage were detectable after just one round of selection, and only these phage remained by the end of the second round, demonstrating the specificity of the selection method. These results indicate a selective enrichment of the U1A-phage of $10^4$–$10^5$ fold per round.

Figure 2:
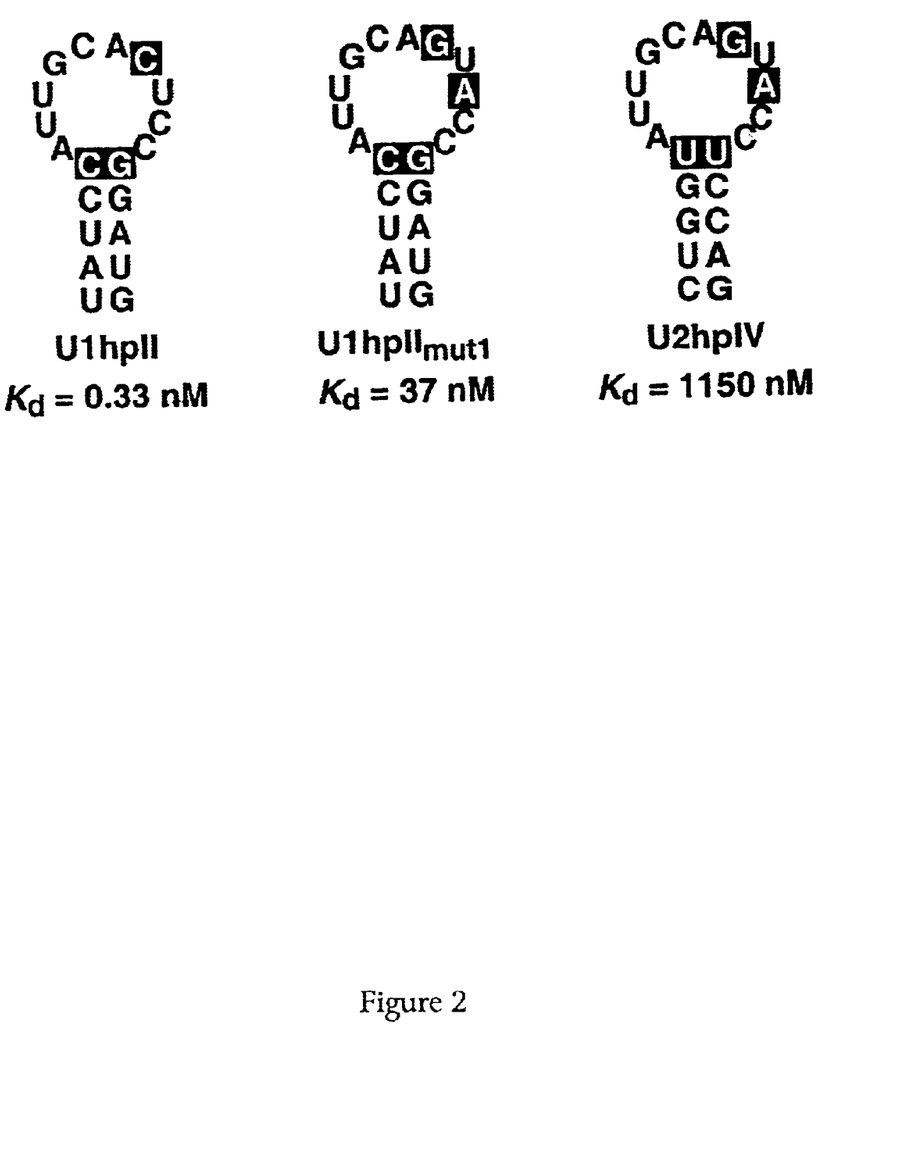

Many RNA-BPs of potential interest would bind their RNA targets with an affinity significantly less than that of U1A for U1hpII. To assess the usefulness of T7 phage display for isolating phage that display proteins with a low RNA-binding affinity such weak interactions were simulated by using low-affinity RNA ligands to select for U1A phage diluted into a $10^6$ fold excess of bare phage. Two such ligands were employed. One was a U1hpII variant (U1hpII$_{mut1}$; FIG. 2) bearing two point mutations that reduce its affinity for U1A by two orders of magnitude ($K_d$=37 nM). The other was a U2 snRNA stem-loop (U2hpIV; FIG. 2) that resembles U1hpII but has a markedly lower affinity for U1A ($K_d$=1150 nM). Three rounds of selection with U1hpII$_{mut1}$ were sufficient to produce a U1A phage signal comparable in strength to that observed after one round with wild-type U1hpII With U2hpIV, a U1A phage signal was detected after four rounds of selection. These findings demonstrate that T7 phage display not only allows the selection of low-affinity RNA-BPs but in addition, an inverse correlation exists between the affinity of an RNA-BP for the RNA bait and the number of selection cycles needed for phage isolation.

Selection of RNA-BP-displaying phage from a lung cDNA library: Next it was determined as to whether U1A phage could be isolated from a complex phage pool displaying an entire cDNA library. A T7 phage display library of human lung cDNAs was constructed by subcloning the cDNA inserts of a commercial oligo(dT)-primed plassid library into an equimolar mixture of three T7 phage vectors, T7Select1-2a, -2b, and -2c, which should allow translation of each cDNA in all three reading frames. The resulting phage library contained $1.2 \times 10^7$ independent recombinants (about twice the complexity of the original plasmid library), with insert sizes of 0.3–3 kb (0.6–0.8 kb on average).

Initial selection from the cDNA library was performed by using U1hpII as bait. After three rounds of selection, a unique clone bearing a 1.1-kb cDNA insert could be detected. Sequence analysis of this insert showed it to comprise the complete coding sequence and 3'-untranslated region of human U1A cDNA. As the U1A RNA-binding domain that recognizes U1hpII is located at the extreme N-terminus of the protein, very few truncated forms of U1A encoded by shorter cDNAs would have been able to bind the RNA bait. Subsequent selection experiments with the low-affinity ligands U1hpII$_{mut1}$ and U2hpIV led to isolation of the same U1A-displaying phage clone, albeit after a greater number of selection cycles.

Surprisingly, phage displaying U2B" were not isolated when using U2hpIV as bait, the natural protein ligand of this snRNA stem-loop (Scherly et al. (1990) Nature 345:502–506; Bentley et al. (1991) Mol. Cell. Biol. 11:1829–1839; Price et al. (1998) Nature 394: 645–650), even though U2B" binds to U2hpIV >200fold more tightly than does U1A (Rimmele et al. (1998) supra). However, PCR analysis with U2B"-specific primers revealed that the T7 cDNA library used in these experiments did not contain a U2B" cDNA clone of sufficient length to be capable of binding U2hpIV.

Figure 3:
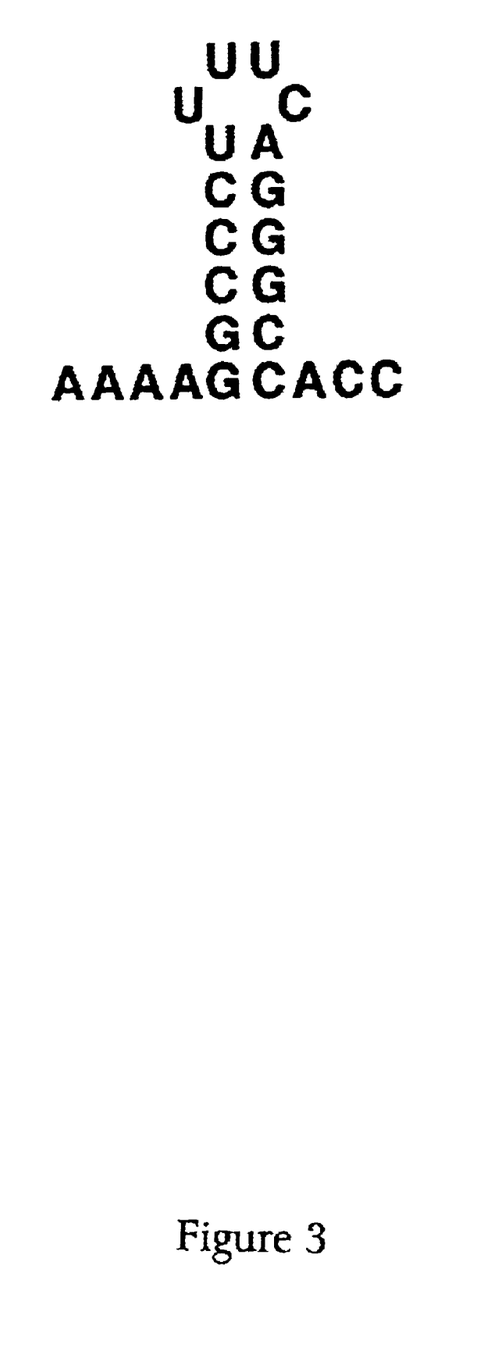
FIG. 3 shows the structure of the 3' histone RNA stem-loop used in the experiment. In addition, this RNA bore a 5' leader and a 3' tail annealed to a complementary biotinylated DNA oligonucleotide (the same as in FIG. 2).
Figure 4:
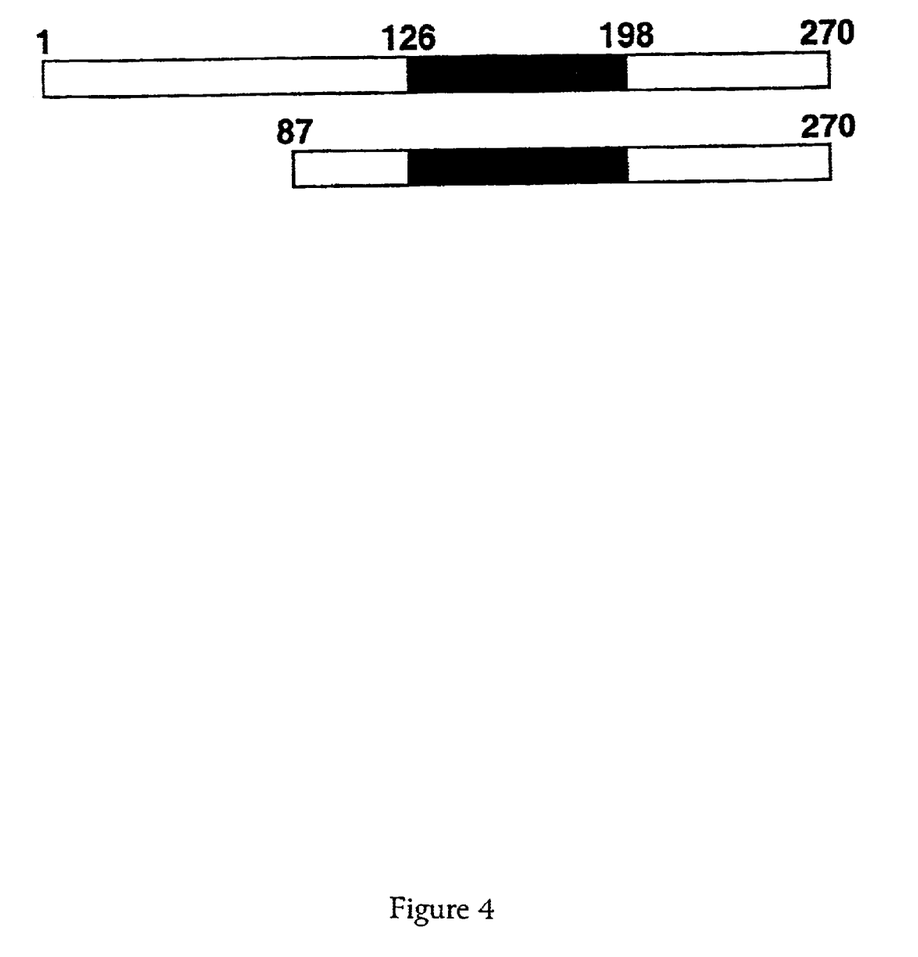
FIG. 4 is a schematic representation of full-length human SLBP (Wang et al. (1996) Genes Dev. 10:3028–3040; Martin et al. (1997) EMBO J. 16:769–77A8) and of the amino-terminally truncated form of SLBP (amino acid residues 87–270) displayed on the surface of the isolated phage clone. The region of SLBP comprising its minimal RNA-binding domain (residues 126–198) is shown in black.

As a further test of the general utility of this method, the sane cDNA library was used to select for phage displaying an RNA-BP of a different type: the histone stem-loop binding protein (SLBP). SLBP is essential for the 3' processing and stability of histone mRNAs, and uses an RNA-binding domain entirely unlike that of U1A to bind a stem-loop near the 3' terminus of these transcripts (FIG. 3) (Dominski et al. (1999) Gene 239:1–14). Three rounds of selection with this stem-loop led to the emergence of a unique phage clone containing a cDNA insert 1.3 kb in length. Sequence analysis revealed that this cDNA encoded amino acid residues 87–270 of human SLBP (FIG. 4) together with the 3'-untranslated region of SLBP mRNA. This portion of SLBP contains the complete RNA-binding domain (residues 126–198), which alone is sufficient to bind the histone mRNA stem-loop with high affinity ($K_d$=4 nM) (Battle et al. (2001) RNA 7:123–132; Michel et al. (2000) RNA 6:1539–1550). PCR and sequence analyses of the cDNA library used for these experiments showed that it contained no other in-frame SLBP clone encoding the RNA-binding domain.

Together, these findings demonstrate that T7 phage display allows the efficient cloning of a variety of RNA-BPs from a complex cDNA library, including those that bind their RNA targets with modest affinities corresponding to $K_d$ values as high as the micromolar range.

Use of a competitor RNA to favor selection of a lower-affinity RNA-BP: A potential impediment to cloning some RNA-BPs on the basis of their RNA-binding specificity is that the RNA ligand of interest may have a greater affinity for a protein other than the one being sought, making it difficult to isolate proteins besides the one with the highest affinity. The control over selection conditions afforded by phage display offers an opportunity to circumvent such complications by using a competitor RNA to sequester the interfering high-affinity protein.

To investigate the feasibility of this approach, U1A and the closely related spliceosomal protein U2B" were used as a model system. U2B" is a homologous spliceosomal protein that uses its amino-terminal RRM domain to bind a U2 snRNA stem-loop (U2hpIV) closely related to U1hpII. A U1hpII variant (U1hpII$_{mut2}$) bearing a single C→G substitution in the loop (AUUGCA<u>C</u>UCC (SEQ ID NO: 16)→AUUGCA<u>G</u>UCC (SEQ ID NO: 17)) binds U1A three times more tightly than U2B" (K$_d$=6 nM for U1A versus 19 nM for U2B") (Rimmele et al. (1998) supra). As expected, when an equimolar mixture of U1A- and U2B"-displaying phage is diluted into a 10$^6$-fold excess of bare T7 phage and subjected to in vitro selection with excess U1hPII$_{mut2}$ (50 nM), both the U1A phage and the U2B" phage are readily amplified (results not shown).

The effect of including an unbiotinylated competitor RNA in the selection mixture was tested next. Wild-type U1hpII binds 15 times more tightly to U1A than to U2B" (K$_d$=0.33 nM for U1A versus 5 nM for U2B") (Rimmele et al. (1998) supra). When selection of the U1A- and U2B"-displaying phage was repeated using a combination of biotinylated U1hpII$_{mut2}$ RNA (bait; 50 nM) and unbiotinylated U1hpII RNA (competitor; 25 nM), the U2B" phage exhibited a marked selective advantage over the U1A phage. This finding demonstrates the possibility of using an RNA competitor to suppress selection of an unwanted high-affinity RNA-BP clone, thereby facilitating the isolation of T7 phage that display RNA-BPs of lower affinity for the RNA bait.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Preparation of recombinant T7 phage: A U1A-displaying phage was constructed in several steps. First, an EcoRI site (5'-GGAATTCC-3') (SEQ ID NO:2) was inserted into the NcoI site (filled in) of the expression vector pU1A101.ex (Laird-Offringa et al. (1995) Proc. Natl. Acad. Sci. USA 92: 11859–11863), which encodes amino acids 1–101 of human U1A preceded by a tether of 10 amino acids (PMAQVQLUVD) (SEQ ID NO:3). A FLAG epitope-tag (DYKDDDDK) (SEQ ID NO:4) was inserted into the NotI site downstream of the U1A cDNA. The resulting EcoRI-NotI restriction fragment was cloned between the corresponding sites of the T7 phage vector T7Select1-2c (Novagen). DNA (1 g) was packaged using a T7 Packaging Extract (Novagen). Phage titers were determined by plaque assays, as described Novagen (2000) T7Select System Manual TB178 (Novagen, Madison, Wis.). The inserts of recombinant clones were examined by heating portions of randomly chosen plaques at 65° C. for 5 min in 10 mM EDTA (50:1) and analyzing the DNA by PCR using a pair of primers that flank the site of cDNA insertion: 5'-GGAGCTGTCGTATTCCAGTC-3' (SEQ ID NO:5) (forward) and 5'-GGCTGATACCACCCTTCAAG-3' (SEQ ID NO:6) (reverse). Recombinant phage were amplified in liquid culture (5 ml), and their identity was confirmed by DNA sequencing. Display of U1A on the phage surface was verified by immunoblot analysis using the M2 anti-FLAG antibody (Sigma) or a monoclonal anti-U1A antibody (MAb 12E12) (O'Connor et al. (1997) RNA 3:1444–1455). The U2B"-displaying phage was identical to the U1A phage except that (i) the U1A cDNA was replaced with a DNA segment encoding amino acids 1–98 of a previously described human U2B" variant bearing eight U1A-derived amino acid substitutions near its carboxyl terminus (Rimmele et al. (1998) RNA 4:1386–1396) and (ii) an untranslated 100-bp spacer was inserted between the NotI and XhoI sites to allow the U2B" phage to be distinguished from U1A phage by PCR.

Construction of a T7 human lung cDNA library: A T7 phage display library of human lung cDNAs was constructed from an existing human lung cDNA plasmid library (display GREEN cDNA library, Display Systems Biotech) generated from WI-38 lung fibroblasts. The cDNA inserts of the plasmid library were excised by digestion with EcoRI and NotI and inserted between the corresponding sites of an equimolar mixture of T7Select1-2a, -2b, and -2c DNA (Novagen) to allow translation of each cDNA in all three reading frames. The resulting phage library had a complexity of 1.2×10$^7$ independent clones, as determined by plaque assays. The library was amplified once by infecting a mid-log-phase E. coli culture (250 ml, OD$_{600}$.0.6) with the phage library at an MOI (multiplicity of infection) of 0.001. After cell lysis, the phage lysate was made 0.5 M in NaCl, clarified by centrifugation, and stored at −80° C. The insert sizes of 64 individual clones as well as of the complete library were analyzed by PCR with the forward primer (SEQ ID NO:5) and the reverse primer (SEQ ID NO:6). The same PCR primers were used to analyze the phage pools isolated after each round of selection from the library.

RNA synthesis: The in vitro transcription templates pEP-U1hpII and pEP-U2hpIV have been described previously (Laird-Offringa et al. (1995) Proc. Natl. Acad. Sci. USA 92:11859–11863), as have the two pEP-U1hpII variants mut1 and mut2 (Rimmele et al. (1998) supra). The DNA template for in vitro synthesis of the histone 3' stem-loop was prepared by inserting a synthetic HindIII-PstI fragment (5'-AAGCTTAAAAGGCCCTTTTCAGGGCCACCCT-GCAG-3') (SEQ ID NO:7) into the polylinker of pT7/T3a-19 (GIBCO-BRL). RNA was synthesized with a T7-MEGAshortscript kit (Ambion), using DNA templates linearized with AvaI and a trace amount of [a-$^{32}$P]CTP to aid in visualization of RNA bands. The radiolabeled transcripts were separated on denaturing 8% polyacrylamide gels, and the RNA bands were excised and eluted overnight in 0.3 mM sodium acetate, pH 5.0, 1 mM EDTA, 0.1% SDS at 37° C. The sequences of the RNAs prepared in this manner and used for in vitro selection were as follows: U1hpII: 5'-GGGAGACCCAAGCUUAUCCAUUGCACUCCGGA-UGAG<u>CUGCAGGUCGACUCUAGAGGAUCCCCGG</u>-3' (SEQ ID NO:8); U2hpIV: 5'-GGAGACCCA-AGCUUCCUGGUAUUGCAGUACCUCCAGGAAG <u>X</u>-3' (SEQ ID NO:9); 3' histone RNA stem-loop: 5'GGAAAGCUUAAAAGGCCCUUUUCAGGGCCACC <u>X</u>-3' (SEQ ID NO: 10) (where <u>X</u> denotes the 3' tail underlined in the U1hpII sequence). The U1hpII$_{mut1}$ and U1hpII$_{mut2}$ RNAs were each identical to U1hpII except for the nucleotide substitutions described above.

Construction of an RNase I-deficient E. coli host strain: A derivative of E. coli BLT5615 (Novagen) lacking the RNase I gene (rna), was generated by P1 transduction from E. coli DK533 (Cannistraro et al. (1991) J. Bacteriol. 173:46534659) and selection for the kanamycin-resistance phenotppe of its Drna::kan allele. The resulting E. coli strain RNA5615 has the genotype F⁻ rna ompT gal hsdS$_B$ (r$_B^-$ m$_B^-$) dcm lac pAR5615 (amp$^R$). Synthesis of the wild-type phage capsid protein encoded by pAR5615 was induced by adding IPTG (1 mM) to the medium about 30 min before phage infection.

RNase I is the protein product of the *E. coli* rna gene. The *E. coli* RNase I amino acid sequence is (SEQ ID NO: 1):

MKAFWRNAALLAVSLLPFSSANALALQAKQY-
GDFDRYVLALSWQTGFCQSQHDRN RNERD-
ECRLQTETTNKDFLTVHGLWPGLPKSVAARG-
VDERRWMRFGCATRPIPNLPEARASRMCS-
SPETGLSLETAAKLSEVMPGAGGRSCLER-
YEYAKHGACFGFDPDAY FGTMVRLNQ-
EIKESEAGKFLADNYGKTVSRRDFDAAFA-
KSWGKENVKAVKLTCQG NPAYLTEIQISIKA-
DAINAPLSANSFLPQPHPGNCGKTFVIDKAGY

For the RNA degradation experiments, purified, radiolabeled RNA (5 pmol) was fixed with a Ti phage lysate [5×10⁹ plaque forming units (pfu)] grown on BLT5615 or RNA5615 and incubated at room temperature. The samples were analyzed by electrophoresis on nondenaturing 8% polyacrylamide gels, and the radioactive bands were visualized with a Molecular Dynamics Phosphorlmager.

Phage affinity selection: Purified RNA was annealed via its 3' tail to a complementary 5'-biotinylated DNA oligonucleotide (5'-ACCGGGGATCCTCTAGAGTC-3') (SEQ ID NO:11). Phage binding experiments were performed in a volume of 60:1 (containing RNA (10–120 nM), T7 phage (1–5×10 pfu), *E. coli* tRNA (50 g, Sigma), and SUPERase.IN (20 U, Ambion) in TENT buffer (10 mM Tris/HCl, pH 8.0, 1 nM EDTA, 250 mM NaCl, 0.5% Triton X-100). After 20 min incubation on a tube rotator at room temperature, the binding reaction was mixed with prewashed streptavidin-coated paramagnetic beads (Dynabeads M-280 Streptavidin, Dynal) and incubated for another 30 min at room temperature to allow the capture of RNA-bound phage on the beads. The beads were separated from the supernatant with a magnet (Dynal), washed twice, and resuspended in TENT buffer. The bound phage were then used without release from the beads to infect a log-phase *E. coli* culture (5 ml), the infected cells lysed within about 2 hours, whereupon the phage lysates were titered via plaque assays, and an aliquot was used for the next round of selection. In vitro selection of phage was monitored by PCR using the procedure and primers described above.

What is claimed is:

1. An *E. coli* cell having the genotype F⁻ rna ompT gal hsdS$_B$ (r$_B$–m$_B$–) dcm lac pAR5615 (amp$^R$).

2. A kit for identifying a nucleic acid that encodes an RNA-binding protein that binds to a specific RNA regulatory element comprising:
   (a) a T7 phage display vector encoding T7 capsid protein 10B;
   (b) an *E.coli* cell having the genotype F⁻ rna ompT gal hsdS$_B$ (r$_B$–m$_B$–) dcm lac pAR5615 (amp$^R$); and
   (c) streptavidin-coated paramagnetic beads.

3. The kit of claim 2 further comprising a protocol for performing the identification.

4. A method of identifying a nucleic acid that encodes an RNA-binding protein that binds to a specific RNA regulatory element comprising:
   (a) inserting a nucleic acid encoding a heterologous protein into a T7 phage display vector, wherein the heterologous protein is expressed as a fusion protein with a phage capsid protein;
   (b) transfecting the T7 phage display vector into a host cell, wherein the host cell has been modified to delete a preselected ribonuclease;
   (c) packaging the phage display vector in a phage capsid in a host cell under conditions which results in lysis of the host cell and formation of a lysate;
   (d) contacting the lysate with a ribonucleotide comprising a specific RNA regulatory element; wherein when a phage capsid comprises a nucleic acid that encodes a heterologous protein that binds the specific RNA regulatory element, the phage capsid binds to the ribonucleotide forming an RNAapsid complex;
   (e) separating the ribonucleotide and the RNA-capsid complex from the lysate; and
   (f) identifying the nucleic acid encoding the heterologous protein of the phage capsid of the RNA-capsid complex; wherein the nucleic acid identified encodes an RNA-binding protein that binds to the specific RNA regulatory element.

5. The method of claim 4, wherein the T7 phage display vector encodes T7 capsid protein 10B.

6. The method of claim 4, wherein the host cell is a Gram negative bacterium.

7. The method of claim 6 wherein the Gram negative bacterium is selected from the group consisting of Enterobacter, Salmonella, Shigella, Yersinia, Klebsiella, and *Escherichia coli*.

8. The method of claim 7 wherein the Gram negative bacterium is *Escherichia coli*.

9. The method of claim 8 wherein the *Escherichia coli* bacterium is modified to lack the gene for ribonuclease Rnase I.

10. The method of claim 9, wherein the *Escherichia coli* bacterium comprises the genotype F– nra ompT gal hsdS$_B$ (r$_{B-}$m$_{B-}$) dcm lac pAR5615 (amp$^R$).

11. A method of identifying a nucleic acid that encodes an RNA-binding protein that binds to a specific RNA regulatory element comprising:
   (a) inserting a cDNA into a T7 phage display vector encoding T7 capsid protein 10B such that a heterologous protein encoded by the cDNA is expressed as a C-terminal fusion protein with T7 capsid protein 10B when the T7 phage display vector is packaged in a phage capsid;
   (b) packaging the T7 phage display vector in a phage capsid in the *E. coli* cell of claim 1 conditions in which the phage capsid lyses the *E. coli* cell forming a lysate;
   (c) contracting the lysate with a ribonucleotide comprising a specific RNA regulatory element; wherein when a phage capsid comprises a nucleic acid that encodes a heterologous proteins that binds the specific RNA regulatory element, the phage capsid binds to the ribonucleotide forming an RNA-capsid complex;
   (d) separating the ribonucleotide and the RNA-capsid complex from the lysate; and
   (e) identifying the nucleic acid encoding the heterologous protein of the phage capsid of the RNA-capsid complex; wherein the nucleic acid identified encodes an RNA-binding protein that binds to the specific RNA regulatory element.

* * * * *

SEQUENCE LISTING

<160> NUMBER OF SEQ ID NOS: 17

<210> SEQ ID NO 1
<211> LENGTH: 268
<212> TYPE: PRT
<213> ORGANISM: Escherichia coli

<400> SEQUENCE: 1

Met Lys Ala Phe Trp Arg Asn Ala Ala Leu Leu Ala Val Ser Leu Leu
1               5                   10                  15

Pro Phe Ser Ser Ala Asn Ala Leu Ala Leu Gln Ala Lys Gln Tyr Gly
            20                  25                  30

Asp Phe Asp Arg Tyr Val Leu Ala Leu Ser Trp Gln Thr Gly Phe Cys
        35                  40                  45

Gln Ser Gln His Asp Arg Asn Arg Asn Glu Arg Asp Glu Cys Arg Leu
    50                  55                  60

Gln Thr Glu Thr Thr Asn Lys Ala Asp Phe Leu Thr Val His Gly Leu
65                  70                  75                  80

Trp Pro Gly Leu Pro Lys Ser Val Ala Ala Arg Gly Val Asp Glu Arg
                85                  90                  95

Arg Trp Met Arg Phe Gly Cys Ala Thr Arg Pro Ile Pro Asn Leu Pro
            100                 105                 110

Glu Ala Arg Ala Ser Arg Met Cys Ser Ser Pro Glu Thr Gly Leu Ser
        115                 120                 125

Leu Glu Thr Ala Ala Lys Leu Ser Glu Val Met Pro Gly Ala Gly Gly
    130                 135                 140

Arg Ser Cys Leu Glu Arg Tyr Glu Tyr Ala Lys His Gly Ala Cys Phe
145                 150                 155                 160

Gly Phe Asp Pro Asp Ala Tyr Phe Gly Thr Met Val Arg Leu Asn Gln
                165                 170                 175

Glu Ile Lys Glu Ser Glu Ala Gly Lys Phe Leu Ala Asp Asn Tyr Gly
            180                 185                 190

Lys Thr Val Ser Arg Arg Asp Phe Asp Ala Ala Phe Ala Lys Ser Trp

-continued

```
                195                 200                 205
Gly Lys Glu Asn Val Lys Ala Val Lys Leu Thr Cys Gln Gly Asn Pro
    210                 215                 220

Ala Tyr Leu Thr Glu Ile Gln Ile Ser Ile Lys Ala Asp Ala Ile Asn
225                 230                 235                 240

Ala Pro Leu Ser Ala Asn Ser Phe Leu Pro Gln Pro His Pro Gly Asn
                245                 250                 255

Cys Gly Lys Thr Phe Val Ile Asp Lys Ala Gly Tyr
            260                 265
```

<210> SEQ ID NO 2
<211> LENGTH: 8
<212> TYPE: DNA
<213> ORGANISM: Escherichia coli

<400> SEQUENCE: 2 ggaattcc                                                              8

<210> SEQ ID NO 3
<211> LENGTH: 10
<212> TYPE: PRT
<213> ORGANISM: Escherichia coli

<400> SEQUENCE: 3

```
Pro Met Ala Gln Val Gln Leu Gln Val Asp
1               5                   10
```

<210> SEQ ID NO 4
<211> LENGTH: 8
<212> TYPE: PRT
<213> ORGANISM: Escherichia coli

<400> SEQUENCE: 4

```
Asp Tyr Lys Asp Asp Asp Asp Lys
1               5
```

<210> SEQ ID NO 5
<211> LENGTH: 20
<212> TYPE: DNA
<213> ORGANISM: Escherichia coli

<400> SEQUENCE: 5
ggagctgtcg tattccagtc                                                20

<210> SEQ ID NO 6
<211> LENGTH: 20
<212> TYPE: DNA
<213> ORGANISM: Escherichia coli

<400> SEQUENCE: 6
ggctgatacc acccttcaag                                                20

<210> SEQ ID NO 7
<211> LENGTH: 35
<212> TYPE: DNA
<213> ORGANISM: Escherichia coli

<400> SEQUENCE: 7
aagcttaaaa ggcccttttc agggccaccc tgcag                               35

<210> SEQ ID NO 8
<211> LENGTH: 64

```
<212> TYPE: DNA
<213> ORGANISM: Escherichia coli

<400> SEQUENCE: 8
gggagaccca agcuuaucca uugcacuccg gaugagcugc aggucgacuc uagaggaucc        60
ccgg                                                                    64

<210> SEQ ID NO 9
<211> LENGTH: 40
<212> TYPE: DNA
<213> ORGANISM: Escherichia coli

<400> SEQUENCE: 9
ggagacccaa gcuuccuggu auugcaguac cuccaggaag                             40

<210> SEQ ID NO 10
<211> LENGTH: 33
<212> TYPE: DNA
<213> ORGANISM: Escherichia coli

<400> SEQUENCE: 10
gggaaagcuu aaaaggcccu uuucagggcc acc                                    33

<210> SEQ ID NO 11
<211> LENGTH: 20
<212> TYPE: DNA
<213> ORGANISM: Escherichia coli

<400> SEQUENCE: 11
accggggatc ctctagagtc                                                   20

<210> SEQ ID NO 12
<211> LENGTH: 20
<212> TYPE: DNA
<213> ORGANISM: Escherichia coli

<400> SEQUENCE: 12
uauccauugc acuccggaug                                                   20

<210> SEQ ID NO 13
<211> LENGTH: 21
<212> TYPE: DNA
<213> ORGANISM: Escherichia coli

<400> SEQUENCE: 13
uauccauugc aguaccggau g                                                 21

<210> SEQ ID NO 14
<211> LENGTH: 21
<212> TYPE: DNA
<213> ORGANISM: Escherichia coli

<400> SEQUENCE: 14
cugguauugc aguaccucca g                                                 21

<210> SEQ ID NO 15
<211> LENGTH: 23
<212> TYPE: DNA
<213> ORGANISM: Escherichia coli

<400> SEQUENCE: 15
aaaaggcccu uuucagggcc acc                                               23
```

```
<210> SEQ ID NO 16
<211> LENGTH: 10
<212> TYPE: DNA
<213> ORGANISM: Escherichia coli

<400> SEQUENCE: 16
auugcacucc                                                              10

<210> SEQ ID NO 17
<211> LENGTH: 10
<212> TYPE: DNA
<213> ORGANISM: Escherichia coli

<400> SEQUENCE: 17
auugcagucc                                                              10
```